(12) United States Patent
Ruskinko et al.

(10) Patent No.: US 6,660,870 B1
(45) Date of Patent: Dec. 9, 2003

(54) 2-ACYLAMINOBENZIMIDAZOLE DERIVATIVES FOR TREATING GLAUCOMA

(75) Inventors: Andrew Ruskinko, Arlington, TX (US); Mark R. Hellberg, Highland Village, TX (US); Namil Abdelmoula, Arlington, TX (US)

(73) Assignee: Alcon, Inc., Hunenberg (CH)

( * ) Notice: Subject to any disclaimer, the term of this patent is extended or adjusted under 35 U.S.C. 154(b) by 0 days.

(21) Appl. No.: 10/221,251

(22) PCT Filed: Nov. 14, 2000

(86) PCT No.: PCT/US00/31260

§ 371 (c)(1),
(2), (4) Date: Sep. 10, 2002

(87) PCT Pub. No.: WO01/70705

PCT Pub. Date: Sep. 27, 2001

Related U.S. Application Data

(60) Provisional application No. 60/190,280, filed on Mar. 17, 2000.

(51) Int. Cl.[7] .............................................. C07D 235/30
(52) U.S. Cl. .................................................... 548/307.4
(58) Field of Search ....................................... 548/307.4

(56) References Cited

U.S. PATENT DOCUMENTS

| | | |
|---|---|---|
| 4,690,931 A | 9/1987 | Wick et al. |
| 5,151,444 A | 9/1992 | Ueno et al. |
| 5,296,504 A | 3/1994 | Stjernschantz et al. |
| 5,352,708 A | 10/1994 | Woodward et al. |
| 5,422,368 A | 6/1995 | Stjernschantz et al. |
| 5,494,928 A | 2/1996 | Bos |
| 5,571,833 A | 11/1996 | Kruse et al. |
| 5,874,477 A | 2/1999 | McConnell et al. |
| 5,889,052 A | 3/1999 | Klimko et al. |
| 5,902,815 A | 5/1999 | Olney et al. |

FOREIGN PATENT DOCUMENTS

| | | |
|---|---|---|
| WO | WO 94/13275 A2 A3 | 6/1994 |
| WO | WO 98/31354 A2 A3 | 7/1998 |
| WO | WO 00/16761 | 3/2000 |

OTHER PUBLICATIONS

Bowen, W. P. and Jerman, J. C., "Nonlinear regression using spreadsheets", Trends Pharmacol. Sci., 16:413–417 (1995).
Database Chemcats; AN 2000:926541, Catalog Name: Ambinter: Screening Collection, Aug. 23, 1999; Benzamide, N–[1–[2–(diethylamino)ethyl]–1H–benzimidazol–2–yl]–3–fluoro–; CAS Registry No.: 296799–22–9.
Database Chemcats; AN 2000:930567; Catalog Name: ChemDiv, Inc. Product Library, Jul. 7, 2000, Benzamide, N–[1–[2–(diethylamino)ethyl]–1N–benzimidazol–2–yl]—; CAS Registry No.: 292613–13–9.
Fiorella, D., et al., "Role of 5–HT2A and 5–HT2C receptors in the stimulus effects of hallucinogenic drugs II: reassessment of LSD false positives", Psychopharmacology, vol. 121:357–363 (1995).
Griffin, B. W., et al., "Pharmacological Characterization of an FP Prostaglandin Receptor on Rat Vascular Smooth Muscle Cells (17r5) Coupled to Phosphoinositide Turnover and Intracellular Calcium Mobilization", J. Pharmacol. Exp. Ther., 286:411–418 (1998).
Johnson, M. P., et al., "Binding To The Serotonin 5–HT2 Receptor By The Enantiomers of 125I–DOI", Neuropharmacology, 26:1803–1806 (1987).
Popov, I. I. and Zubenko, A. A., "Investigations Of Unsaturated Azoles. 15. *Synthesis And Reactions Of Acylated Benzimidazoles", Chemistry of Heterocyclic Compounds, 33:293–299 (1997).
Settimo et al: "Synthesis, DNA binding and in vitro antiproliferative activity of purinoquinazoline, pyridopyrimidopurine and pyridopyrimidobenzimidazole derivatives as potential antitumor agents", Eur. J. Med. Chem. (1998), 33(9), 685–696.
Sugrue M.F. "New Approaches To Antiglaucoma Therapy", Journal of Medicinal Chemistry, US, American Chemical Society, Washington, vol. 40, No. 18, Aug. 29, 1997, pp. 2793–2809.

*Primary Examiner*—Patricia L. Morris
(74) *Attorney, Agent, or Firm*—Teresa J. Schultz

(57) ABSTRACT

2-Acylaminobenzimidazole deviates useful for treating glaucoma are disclosed.

2 Claims, No Drawings

2-ACYLAMINOBENZIMIDAZOLE DERIVATIVES FOR TREATING GLAUCOMA

This application is a 371 of PCT/US00/31260 filed on Nov. 14, 2000, and U.S. Ser. No. 60/190,280, filed on Mar. 17, 2000.

The present invention is directed to novel substituted 2-acylaminobenzimidazoles and the use of novel and known 2-acylaminobenzimidazoles for lowering and controlling normal or elevated intraocular pressure (IOP) and treating glaucoma.

BACKGROUND OF THE INVENTION

The disease state referred to as glaucoma is characterized by a permanent loss of visual function due to irreversible damage to the optic nerve. The several morphologically or functionally distinct types of glaucoma are typically characterized by elevated IOP, which is considered to be causally related to the pathological course of the disease. Ocular hypertension is a condition wherein intraocular pressure is elevated, but no apparent loss of visual function has occurred; such patients are considered to be a high risk for the eventual development of the visual loss associated with glaucoma. Some patients with glaucomatous field loss have relatively low intraocular pressure. These so called normotension or low tension glaucoma patients can also benefit from agents that lower and control IOP. If glaucoma or ocular hypertension is detected early and treated promptly with medications that effectively reduce elevated intraocular pressure, loss of visual function or its progressive deterioration can generally be ameliorated. Drug therapies that have proven to be effective for the reduction of intraocular pressure include both agents that decrease aqueous humor production and agents that increase the outflow facility. Such therapies are in general administered by one of two possible routes, topically (direct application to the eye) or orally.

There are some individuals who do not respond well when treated with certain existing glaucoma therapies. There is, therefore, a need for other topical therapeutic agents that control IOP.

It has been found that serotonergic compounds which possess agonist activity at $5\text{-HT}_2$ receptors effectively lower and control normal and elevated IOP and are useful for treating glaucoma, see commonly owned co-pending application, PCT/US99/19888. Compounds that act as agonists at $5\text{-HT}_2$ receptors are well known and have shown a variety of utilities, primarily for disorders or conditions associated with the central nervous system (CNS). U.S. Pat. No. 5,494,928 discloses certain 2-(indol-1-yl)-ethylamine derivatives that are $5\text{-HT}_{2C}$ agonists for the treatment of obsessive compulsive disorder and other CNS derived personality disorders. U.S. Pat. No. 5,571,833 discloses tryptamine derivatives that are $5\text{-HT}_2$ agonists for the treatment of portal hypertension and migraine. U.S. Pat. No. 5,874,477 discloses a method for treating malaria using $5\text{-HT}_{2A/2C}$ agonists. U.S. Pat. No. 5,902,815 discloses the use of $5\text{-HT}_{2A}$ agonists to prevent adverse effects of NMDA receptor hypo-function. WO98/31354A2 discloses $5\text{-HT}_{2B}$ agonists for the treatment of depression and other CNS conditions. Agonist response at the $5\text{-HT}_{2A}$ receptor is reported to be the primary activity responsible for hallucinogenic activity, with some lesser involvement of the $5\text{-HT}_{2C}$ receptor possible [Psychopharmacology, Vol. 121:357, 1995].

Certain 2-acylamino benzimidazole analogs have been reported [*Chemistry of Heterocyclic Compounds* 33, 293 (1997), *Eur. J. Med. Chem.* 33, 685 (1998)]. No utility has been associated with these compounds.

SUMMARY OF THE INVENTION

The present invention is directed to derivatives of 2-acylaminobenzimidazole which can be used to lower and control IOP associated with normal-tension glaucoma, ocular hypertension, and glaucoma in warm blooded animals, including man (Compounds). The compounds are formulated in pharmaceutical compositions suitable for topical delivery to the eye.

DESCRIPTION OF THE PREFERRED EMBODIMENTS

Compounds that are useful for lowering and controlling normal or elevated intraocular pressure (IOP) and treating glaucoma according to the present invention are represented by the following Formula I.

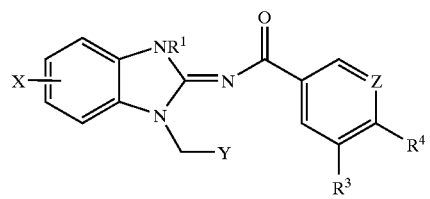

Wherein:

X=H, F, Cl, Br, $OR^1$, CN, C(=O)$R^1$, C(=O)$NR^1R^2$, $C_{1-6}$ alkyl, OC(=O)$R^1$, OC(=O)$NR^1R^2$, or $CF_3$;

R, $R^1$, $R^2$=H or $C_{1-6}$alkyl;

Y=$CH_2NRR^2$ or $CHR^1NRR^2$,

Z=CH or N $R^3$=H, F, Cl, Br, $OR^1$, CN, $C_{1-6}$ alkyl or $CF_3$; and $R^4$=H, $C_{1-3}$ alkyl, F, Cl, Br, I or $CF_3$.

The preferred compounds are those in which: X=H, F, Cl, Br, $OR^1$, or $C_{1-3}$ alkyl, and $R^1$=H, Z=CH.

The most preferred compounds are those wherein: X=H, F, Cl, Br, $OR^1$, $C_{1-3}$ alkyl, or $CF_3$; R and $R^2$=$CH_2CH_3$; and $R^4$=$CH_3$, Z=CH.

Novel compounds are represented by the following Formula I.

Scheme 1

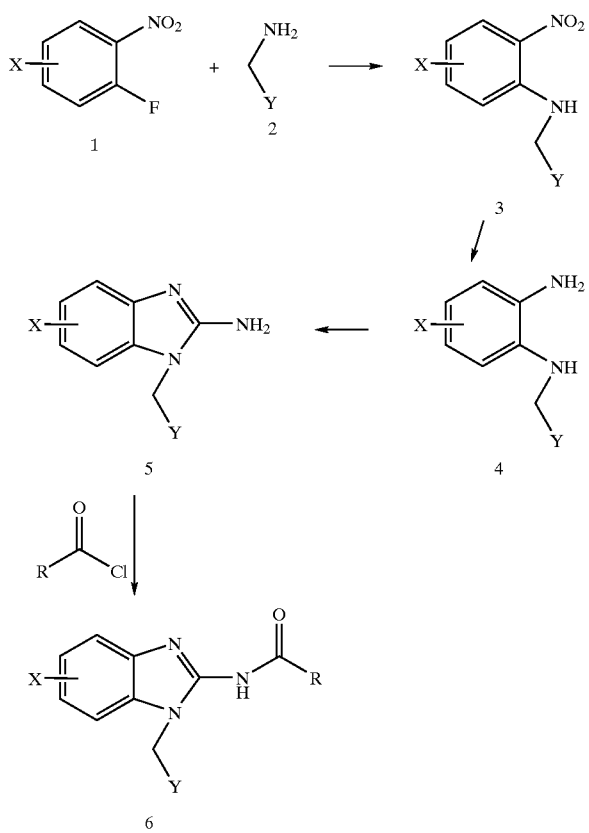

Wherein:
X=H, F, Cl, Br, $OR^1$, CN, $C(=O)R^1$, $C(=O)NR^1R^2$, $C_{1-6}$ alkyl, $OC(=O)R^1$, $OC(=O)NR^1R^2$, or $CF_3$;

R, $R^1$, $R^2$=H or $C_{1-6}$alkyl;

Y=$CH_2NRR^2$ or $CHR^1NRR^2$ or with the proviso that when X=H, Y does not equal $CH_2N(CH_2CH_3)_2$;

Z=CH or N $R^3$=H, F, Cl, Br, $OR^1$, CN, $C_{1-6}$ alkyl or $CF_3$; and $R^4$=H, $C_{1-3}$ alkyl, F, Cl, Br, I or $CF_3$.

It is recognized that compounds of Formula I can contain one or more chiral centers. This invention contemplates all enantiomers, diastereomers, and mixtures thereof.

In the above definitions, the total number of carbon atoms in a substituent group is indicated by the $C_{i-j}$ prefix where the numbers i and j define the number of carbon atoms; this definition includes straight chain, branched chain, and cyclic alkyl or (cyclic alkyl)alkyl groups.

It is important to recognize that a substituent may be present either singly or multiply when incorporated into the indicated structural unit. For example, the substituent halogen, which means fluorine, chlorine, bromine, or iodine, would indicate that the unit to which it is attached may be substituted with one or more halogen atoms, which may be the same or different.

SYNTHESIS

The desired substituted 2-acylaminobenzimidazoles can be prepared by the method below outlined:

The appropriately substituted 2-nitrofluorobenzene 1 is reacted with the aminoalkylamine derivative 2. Reduction of the resulting nitroaniline 3 by catalytic hydrogenation (Pd/C, $H_2$) or by reaction with dithionite yields the diamine 4. Cyclization with cyanogen bromide leads to the desired 2-aminobenzimidazole 5. Acylation of the 2-aminobenzimidazole derivative 5 with an acid chloride in the presence of a base such as triethylamine provides the desired 2-acylaminobenzimidazole 6. The modification of the described synthetic method by the use of certain protecting groups as appropriate can be readily accomplished by one skilled in the art.

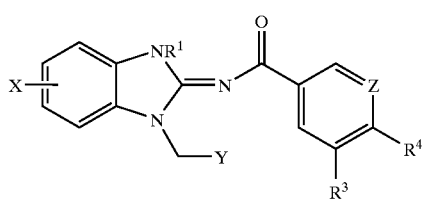

I

The Compounds of this invention, can be incorporated into various types of ophthalmic formulations for delivery to the eye (e.g., topically, intracamerally, or via an implant). The Compounds are preferably incorporated into topical ophthalmic formulations for delivery to the eye. The Compounds may be combined with ophthalmologically acceptable preservatives, surfactants, viscosity enhancers, penetration enhancers, buffers, sodium chloride, and water to form an aqueous, sterile ophthalmic suspension or solution. Ophthalmic solution formulations may be prepared by dissolving a Compound in a physiologically acceptable isotonic aqueous buffer. Further, the ophthalmic solution may include an ophthalmologically acceptable surfactant to assist in dissolving the Compound. Furthermore, the ophthalmic solution may contain an agent to increase viscosity, such as, hydroxymethylcellulose, hydroxyethylcellulose, hydroxypropylmethylcellulose, methylcellulose, polyvinylpyrrolidone, or the like, to improve the retention of the formulation in the conjunctival sac. Gelling agents can also be used, including, but not limited to, gellan and xanthan gum. In order to prepare sterile ophthalmic ointment formulations, the active ingredient is combined with a preservative in an appropriate vehicle, such as, mineral oil, liquid lanolin, or white petrolatum. Sterile ophthalmic gel formulations may be prepared by suspending the Compound in a hydrophilic base prepared from the combination of, for example, carbopol-974, or the like, according to the published formulations for analogous ophthalmic preparations; preservatives and tonicity agents can be incorporated.

The Compounds are preferably formulated as topical ophthalmic suspensions or solutions, with a pH of about 4 to 8. The Compounds will normally be contained in these formulations in an amount 0.01% to 5% by weight, but preferably in an amount of 0.1% to 2% by weight. Thus, for topical presentation 1to 2 drops of these formulations would be delivered to the surface of the eye 1 to 4 times per day according to the discretion of a skilled clinician.

The compounds can also be used in combination with other agents for treating glaucoma, such as, but not limited to, β-blockers (e.g., timolol, betaxolol, levobetaxolol, carteolol, levobunolol, propranolol), carbonic anhydrase inhibitors (e.g., brinzolamide and dorzolamide), $\alpha_1$ antagonists (e.g. nipradolol), $\alpha_2$ agonists (e.g., iopidine and brimonidine), miotics (e.g., pilocarpine and epinephrine), prostaglandin analogs (e.g., latanoprost, travaprost, unoprostone, and compounds set forth in U.S. Pat. Nos. 5,889,052; 5,296,504; 5,422,368; and 5,151,444, "hypotensive lipids" (e.g., lumigan and compounds set forth in U.S. Pat. No. 5,352,708), and neuroprotectants (e.g., compounds from U.S. Pat. No. 4,690,931, particularly eliprodil and R-eliprodil, as set forth in a pending application U.S. Ser. No. 60/203,350, and appropriate compounds from WO94/13275, including memantine.

The following methods can be used to characterize Compounds of the present invention. The examples are given to illustrate the preparation of Compounds but 30 should not be construed as implying any limitations to the claims. The preferred Compound of Formula I is described in Example 1.

METHOD 1

5-HT$_2$ Receptor Binding Assay

In order to determine the relative affinities of serotonergic compounds at the 5-HT$_2$ receptors, their ability to compete for the binding of the agonist radioligand [$^{125}$I]DOI to brain 5-HT$_2$ receptors is determined as described below with minor modification of the literature procedure [Neuropharmacology, 26, 1803 (1987)]. Aliquots of post mortem rat or human cerebral cortex homogenates (400 μl) dispersed in 50 mM TrisHCl buffer (pH 7.4) are incubated with [$^{125}$I]DOI (80 pM final) in the absence or presence of methiothepin (10 μM final) to define total and non-specific binding, respectively, in a total volume of 0.5 ml. The assay mixture is incubated for 1 hour at 23° C. in polypropylene tubes and the assays terminated by rapid vacuum filtration over Whatman GF/B glass fiber filters previously soaked in 0.3% polyethyleneimine using ice-cold buffer. Test compounds (at different concentrations) are substituted for methiothepin. Filter-bound radioactivity is determined by scintillation spectrometry on a beta counter. The data are analyzed using a non-linear. iterative curve-fitting computer program [Trends Pharmacol. Sci., 16, 413 (1995)] to determine the compound affinity parameter. The concentration of the compound needed to inhibit the [$^{125}$I]DOI binding by 50% of the maximum is termed the IC$_{50}$ or K$_i$ value.

METHOD 2

5-HT$_2$ Functional Assay: Phosphoinositide (PI) Turnover Assay

The relative agonist activity of serotonergic compounds at the 5-HT$_2$ receptor can be determined in vitro using the ability of the compounds to stimulate the production of [$^3$H]inositol phosphates in [$^3$H]myo-inositol-labeled A7r5 rat vascular smooth muscle cells by their ability to activate the enzyme phospholipase C. These cells are grown in culture plates, maintained in a humidified atmosphere of 5% CO$_2$ and 95% air and fed semi-weekly with Dulbecco's modified Eagle medium (DMEM) containing 4.5 g/l glucose and supplemented with 2 mM glutamine, 10 μg/ml gentamicin, and 10% fetal bovine serum. For the purpose of conducting the phosphoinositide (PI) turnover experiments, the A7r5 cells are cultured in 24-well plates as previously [J. Pharmacol. Expt. Ther., 286, 411 (1998)]. Confluent cells are exposed for 24–30 hrs to 1.5 μCi [$^3$H]-myo-inositol (18.3 Ci/mmol) in 0.5 ml of serum-free medium. Cells are then rinsed once with DMEM/F-12 containing 10 mM LiCl prior to incubation with the test agent (or solvent as the control) in 1.0 ml of the same medium for 1 hr at 37° C., after which the medium is aspirated and 1 ml of cold 0.1 M formic acid added to stop the reaction. The chromatographic separation of [$^3$H]-inositol phosphates ([$^3$H]-IPs) on an AG-1-X8 column is performed as previously described [J. Pharmacol. Expt. Ther. 286, 411 (1998)] with sequential washes with H$_2$O and 50 mM ammonium formate, followed by elution of the total [$^3$H]-IPs fraction with 1.2 M ammonium formate containing 0.1 M formic acid. The eluate (4 ml) is collected, mixed with 15 ml scintillation fluid, and the total [$^3$H]-IPs determined by scintillation counting on a beta-counter. Concentration-response data are analyzed by the sigmoidal fit function of the Origin Scientific Graphics software (Microcal Software, Northampton, Mass.) to determine agonist potency (EC$_{50}$ value) and efficacy (E$_{max}$). Serotonin (5-HT) is used as a positive control (standard) agonist compound and the efficacy of test compounds is compared to that of 5-HT (set at 100%). The concentration of the compound needed to stimulate the production of [3H]-IPs by 50% of the maximum response is termed the EC$_{50}$ value. Compounds are considered potent agonists if their EC$_{50}$ values in this functional assay are ≦1 μM and are considered is full agonists if their efficacy is >80% of that of 5-HT.

The above procedures were used to generate the data shown in Table 1.

TABLE 1

5-HT2 Receptor Binding and Functional Data.

| Compound | IC$_{50}$, nM | EC$_{50}$, nM | Efficacy (E$_{max}$, %) |
| --- | --- | --- | --- |
| (R)-DOI | 0.46 | 277 | 82 |
| Example 1 | 330 | 404 | 35 |

METHOD 3

Acute IOP Response in Lasered (Hypertensive) Eyes of Conscious Cynomolgus Monkeys Intraocular pressure (IOP) can be determined with an Alcon Pneumatonometer after light corneal anesthesia with 0.1% proparacaine. Eyes are washed with saline after each measurement. After a baseline IOP measurement, test compound is instilled in one 30 μL aliquot to the right eyes only of nine cynomolgus monkeys. Vehicle is instilled in the right eyes of six additional animals. Subsequent IOP measurements are taken at 1, 3, and 6 hours.

EXAMPLE 1

1-(N,N-Dimethylaminoethyl)-2-(4-methylbenzamido)benzimidazole

Step A. 1-(N,N-Dimethylaminoethyl)-2-aminobenzimidazole

2-Fluoronitroberzene (2.00 g, 14.17 mmol) was dissolved in DMF (20 mL) at room temperature, to this solution was added $K_2CO_3$ (2.93 g, 21.24 mmol) followed by N,N-dimethylethylendiamine (1.87 g, 21.26 mmol). The reaction mixture was stirred overnight, diluted with $H_2O$ (100 mL) and then extracted with ethyl acetate. The organic layer was dried ($MgSO_4$) and evaporated to give an orange oil (4.5 g). $^1$H NMR ($CDCl_3$): δ 2.2 (6H, $2CH_3$), 2.51(m, 2H, $CH_2$), 3.35 (m, 2H, $CH_2$), 6.64 (m, 1H), 7.01(d, 1H), 7.54 (m, 1H), 7.95 (d, 1H), 8.28(m, NH). This material was dissolved in ethanol (50 mL) and 0.5 g of Pd/C 10% was added. The mixture was subjected to hydrogenation. Starting material was consumed (TLC) after 2 h. Filtration of the catalyst and evaporation of the solvent gave an oily residue (1 g, 5.58 mmol) which was dissolved in $CH_2Cl_2$ (100 mL). To this solution was added BrCN (2.23 mL of 3M solution in $CH_2Cl_2$) dropwise at room temperature. The reaction mixture was stirred overnight and the solvent was evaporated. The residue was purified by flash chromatography using methanol-triethylamine (5%) to give 0.5 g of the desired material. MS 204 (m+1). $^1$HNMR (DMSO): δ 2.22 (s, 6H, $2CH_3$),2.65(m, $CH_2$), 4.24 (t, $CH_2$), 6.66 (s, $NH_2$) 7.10 (m, 2H), 7.32 (m, 2H).

Analysis for $C_{11}H_{16}N_4$+0.2 $H_2O$. Calculated: C 63.56, H 7.95, N 7.60. Found: C 63.15, H 7.59, N 7.59.

Step B. 1-(N,N-Dimethylaminoethyl)-2-(4-methylbenzamido)benzimidazole 1-(N,N-Dimethylaminoethyl)-2-aminobenzimidazole (0.40 g, 1.96 mmol) was dissolved in $CH_2Cl_2$ (50 mL) and cooled to 0° C., triethylamine (2 mL) was added followed by 4-methylbenzoyl chloride (0.26 g, 1.96 mmol). The reaction mixture was stirred at 0° C. for 1 h and at room temperature for an additional 1 h. The volatiles were evaporated and then the residue was purified by column chromatography using $CH_2Cl_2$-MeOH (9.8–0.2). The oily material collected (0.2 g) was dissolved in anhydrous ethyl ether and transformed to the hydrochloride salt. MS 322 (M+1). $^1$H NMR (DMSO): δ 2.48 (s, 3H), 2.81 and 2.86 (2s, 6H), 3.54 (m, 2H), 4.73 (m, 2H), 35 7.34 (m, 4H), 7.52 (2m, 2H), 8.14 (d, 2H), 10.79 (broad s, NH).

Analysis for $C_{19}H_{22}N_4O$+2HCl+0.3 $H_2O$. Calculated: C 55.21, H 6.34, N 13.55. Found: C 54.94, H 6.55, N 13.32.

EXAMPLE 2

1-(2-Aminopropyl)-2-(4-methylbenzamido)benzimidazole

Step A. 1-(2-tert-Butoxy carbonyl aminopropyl)-2-aminobenzimidazole Hydrobromide 1-(2-tert-Butoxy carbonyl aminopropyl)-2-aminobenzimidazole hydrobromide was prepared by the method of Example 1 using 2-tert-butoxycarbonyl aminopropylamine and 2-fluoro-nitrobenzene as starting materials. The cyclization reaction using cyanogen bromide gave the desired material as a solid which was collected by filtration MS 290 (M+1). $^1$H NMR (DMSO): δ 0.74 (s, 9H,) 0.96 (d, 3H), 3.67 (m, 3H), 6.57 (d, 1H), 7.03(m, 3H), 8.44 (s, 2H, $NH_2$), 12.35 (broad s, NH).

Step B. 1-(2-Aminopropyl)-2-(4-methylbenzamido)benzimidazole

To a solution of 1-(2-tert-butoxyaminopropyl)-2-aminobenzimidazole hydrobromide (1.00 g, 2.70 mmol) and triethylamine (1.9 mL, 3.79 mmol) in $CH_2Cl_2$ (50 mL) was added 4-methylbenzoyl chloride (0.46 g, 29.73 mmol) at 0° C. This mixture was stirred at 0° C. for 1 h and at room temperature overnight. The volatiles were evaporated and the residue was purified by flash chromatography using ethyl acetate-hexane (1:1). The fractions collected were concentrated in vacuo and the residue was dissolved in trifluoroacetic acid (5 ml) and stirred overnight. The trifluoroacetic acid was evaporated and the residue was dissolved in ethyl acetate and washed with a saturated solution of bicarbonate. Ethyl acetate was evaporated and the residue was purified by flash chromatography using $CH_2Cl_2$-MeOH (9.5: 0.5). The oil recovered after evaporation of solvent was transformed to the hydrochloride salt. MS 308 (M+1). $^1$HNMR (DMSO): δ 1.3(d, 3H), 2.37 (s, $CH_3$), 3.80 (m, 1H), 4.45 (m, 2H), 7.26 (m, 4H), 7.55 and 7.62 (2d, 2H), 8.15 (d, 2H), 11.61 (bs, NH).

Analysis for $C_{18}H_{20}N_4O$+2HCl+0.1 $H_2O$. Calculated: C 56.43, H 5.84, N 14.62. Found: C 56.26, H 5.77, N 14.50.

EXAMPLE 3

1-(N,N-Diethylaminoethyl)-2-(4-methylbenzamido)-6-methoxybenzimidazole

Step A. 1-(N,N-Diethylaminoethyl)-2-amino-6-methoxybenzimidazole 1-(N,N-Diethylaminoethyl)-2-amino-6-methoxybenzimidazole was prepared by the method of Example 1 using 2-fluoro-4-methoxybenzimidazole and N,N-diethylethylenediamine as starting materials. MS 262 (M+1). $^1$H NMR (DMSO): δ 1.00 (t, 6H, $2CH_3$), 2.55(m, 4H, $2CH_2$), 2.72 (t, $CH_2$), 3.11 (m, 2H, $CH_2$), 3.75 (s, 3H, $CH_3O$), 6.65 (s, 2H, $NH_2$), 6.14–6.64 (m, 3H).

Step B. 1-(N,N-Diethylaminoethyl)-2-(4-methylbenzamido)-6-methoxybenzimidazole 1-(N,N-Diethylaminoethyl)-2-(4-methylbenzamido)-6-methoxybenzimidazole was prepared by the method of Example 2 using 1-(N,N-diethylaminoethyl)-2-amino-6-methoxybenzimidazole and 4-methylbenzoyl chloride. $^1$H NMR (DMSO): δ 1.33(t, 6H), 2.51 (s, $CH_3$ ar), 3.40 (m, 4H), 3.58 (m, 2H), 3.98 (s, 3H), 4.87 (m 2H), 6.99–8.28 (4 m, 7 H), 11.61 (broad s, NH).

Analysis for $C_{22}H_{28}N_4O_2$+2HCl+0.2 $H_2O$. Calculated: C 53.99, H 7.00, N 11.45. Found:C54.17, H 7.05, N11.45.

EXAMPLE 4

1-(N,N-Dimethylaminoethyl)-2-benzamidobenzimidazole Hydrochloride 1-(N,N-Dimethylaminoethyl)-2-benzamidobenzimidazole hydrochloride was prepared by the method of Example 1 using benzoyl chloride and 1-(N,N-dimethylaminoethyl)-2-aminobenzimidazole. MS 308 (M+1). $^1$H NMR (DMSO): δ 2.92 (s, 3H), 2.94 (s, 3H), 3.60 (m, 2H), 4.75 (m, 2H), 7.27–8.33 (m, 9H), 10.81 (broad s, NH).

Analysis for $C_{18}H_{20}N_4O+2HCl+0.7\ H_2O$. Calculated: C 54.88, H 5.99, N 14.22. Found: C 54.65, H 6.14, N 14.12.

EXAMPLE 5

1-(N,N-Dimethylaminoethyl)-2-(2-thiophenecarboxamido)benzimidazole Hydrochloride 1-(N,N-Dimethylaminoethyl)-2-aminobenzimidazole hydrochloride was prepared by the method of Example 1 using thiophenecarbonyl chloride and 1-(N,N-dimethylaminoethyl)-2-aminobenzimidazole. MS 314 (M +1). $^1$H NMR (DMSO): δ 2.95 (s, 3H), 2.97 (s, 3H), 3.57 (m, 2H), 4.70 (m, 2H), 6.08–7.89 (m, 7H), 10.66 (broad s, NH).

Analysis for $C_{16}H_{18}N_4OS+2HCl+0.2\ H_2O$ calculated: C 49.16, H 5.26, N 14.16. Found: C 48.88, H 5.36, N 14.33.

The following topical ophthalmic formulations are useful according to the present invention administered 1–4 times per day according to the discretion of a skilled clinician.

EXAMPLE 6

| Ingredients | Amount (wt %) |
| --- | --- |
| Compound of Example 3 | 0.1–2% |
| Hydroxypropyl methylcellulose | 0.5% |
| Dibasic sodium phosphate (anhydrous) | 0.2% |
| Sodium chloride | 0.5% |
| Disodium EDTA (Edetate disodium) | 0.01% |
| Polysorbate 80 | 0.05% |
| Benzalkonium chloride | 0.01% |
| Sodium hydroxide/Hydrochloric acid | For adjusting pH to 7.3–7.4 |
| Purified water | q.s. to 100% |

EXAMPLE 7

| Ingredients | Amount (wt %) |
| --- | --- |
| Compound of Example 1 | 0.1–2% |
| Methyl cellulose | 4.0% |
| Dibasic sodium phosphate (anhydrous) | 0.2% |
| Sodium chloride | 0.5% |
| Disodium EDTA (Edetate disodium) | 0.01% |
| Polysorbate 80 | 0.05% |
| Benzalkonium chloride | 0.01% |
| Sodium hydroxide/Hydrochloric acid | For adjusting pH to 7.3–7.4 |
| Purified water | q.s. to 100% |

EXAMPLE 8

| Ingredients | Amount (wt %) |
| --- | --- |
| Compound of Example 3 | 0.1–2% |
| Guar gum | 0.4–6.0% |
| Dibasic sodium phosphate (anhydrous) | 0.2% |
| Sodium chloride | 0.5% |
| Disodium EDTA (Edetate disodium) | 0.01% |
| Polysorbate 80 | 0.05% |
| Benzalkonium chloride | 0.01% |
| Sodium hydroxide/Hydrochloric acid | For adjusting pH to 7.3–7.4 |
| Purified water | q.s. to 100% |

EXAMPLE 9

| Ingredients | Amount (wt %) |
| --- | --- |
| Compound of Example 1 | 0.1–2% |
| White petrolatum and mineral oil and lanolin | Ointment consistency |
| Dibasic sodium phosphate (anhydrous) | 0.2% |
| Sodium chloride | 0.5% |
| Disodium EDTA (Edetate disodium) | 0.01% |
| Polysorbate 80 | 0.05% |
| Benzalkonium chloride | 0.01% |
| Sodium hydroxide/Hydrochloric acid | For adjusting pH to 7.3–7.4 |

We claim:
1. A compound of the formula:

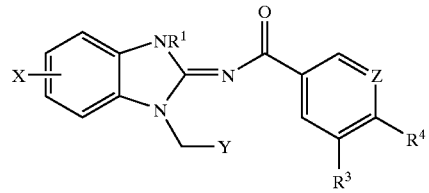

wherein:
X=H, F, Cl, Br, $OR^1$, CN, $C(=O)R^1$, $C(=O)NR^1R^2$, $C_{1-6}$ alkyl, $OC(=O)R^1$, $OC(=O)NR^1R^2$, or $CF_3$;
R, $R^1$, $R^2$=H or $C_{1-6}$alkyl;
Y=$CH_2NRR^2$ or $CHR^1NRR^2$ or with the proviso that when X=H, Y does not equal $CH_2N(CH_2CH_3)_2$;
Z=CH;
$R^3$=H, F, Cl, Br, $OR^1$, CN, $C_{1-6}$ alkyl or $CF_3$; and
$R^4$=H, $C_{1-3}$ alkyl, F, Cl, Br, I or $CF_3$.
2. The compound of claim 1 that is 1-(2-aminopropyl)-2-(4-methylbenzamido)benzimidazole.

* * * * *

UNITED STATES PATENT AND TRADEMARK OFFICE
CERTIFICATE OF CORRECTION

PATENT NO. : 6,660,870 B1
DATED : December 9, 2003
INVENTOR(S) : Rusinko et al.

It is certified that error appears in the above-identified patent and that said Letters Patent is hereby corrected as shown below:

<u>Title page,</u>
Item [75], Inventors, "Andrew Ruskinko" should be -- Andrew Rusinko --; and "Namil Abdelmoula" should be -- Abdelmoula Namil --

Signed and Sealed this

Fifth Day of April, 2005

JON W. DUDAS
*Director of the United States Patent and Trademark Office*